(12) United States Patent
Antonsson et al.

(10) Patent No.: US 7,951,195 B2
(45) Date of Patent: *May 31, 2011

(54) ANNULOPLASTY INSTRUMENT

(75) Inventors: Per Antonsson, Malmö (SE); Paul A. Spence, Louisville, KY (US)

(73) Assignee: Medtentia International Ltd. OY, Helsinki (FI)

( * ) Notice: Subject to any disclaimer, the term of this patent is extended or adjusted under 35 U.S.C. 154(b) by 907 days.

This patent is subject to a terminal disclaimer.

(21) Appl. No.: 11/667,335

(22) PCT Filed: Jun. 15, 2005

(86) PCT No.: PCT/SE2005/000909
§ 371 (c)(1),
(2), (4) Date: May 9, 2007

(87) PCT Pub. No.: WO2006/054930
PCT Pub. Date: May 26, 2006

(65) Prior Publication Data
US 2008/0033542 A1 Feb. 7, 2008

(51) Int. Cl.
*A61F 2/24* (2006.01)
(52) U.S. Cl. ...................................... 623/2.11

(58) Field of Classification Search .................. 623/2.11, 623/2.36, 2.4; 606/99, 139
See application file for complete search history.

(56) References Cited

U.S. PATENT DOCUMENTS

| 5,403,305 A | 4/1995 | Sauter et al. |
| 6,406,492 B1 | 6/2002 | Lytle |
| 6,419,696 B1 * | 7/2002 | Ortiz et al. ............... 623/2.37 |
| 7,077,861 B2 * | 7/2006 | Spence ..................... 623/2.11 |
| 2002/0013621 A1 | 1/2002 | Stobie et al. |
| 2004/0019357 A1 | 1/2004 | Campbell et al. |

FOREIGN PATENT DOCUMENTS
WO    WO 2004/089250 A1    10/2004

* cited by examiner

*Primary Examiner* — Bruce E Snow
(74) *Attorney, Agent, or Firm* — Inskeep IP Group, Inc.

(57) ABSTRACT

A device for repairing a heart valve comprises an implantation instrument. The implantation instrument comprises a first support ring, and a second support ring connected to said first support ring to form a coiled configuration. The first support ring is configured to abut one side of the valve and the second support ring is configured to abut an opposite side of the valve to thereby trap a portion of the valve tissue therebetween. The device further comprises an annuloplasty implant adapted to be attached to the heart valve annulus in order to reshape the annulus and allow the leaflets to open and close properly. The annuloplasty implant is connected to the implantation instrument for insertion to the annulus.

19 Claims, 10 Drawing Sheets

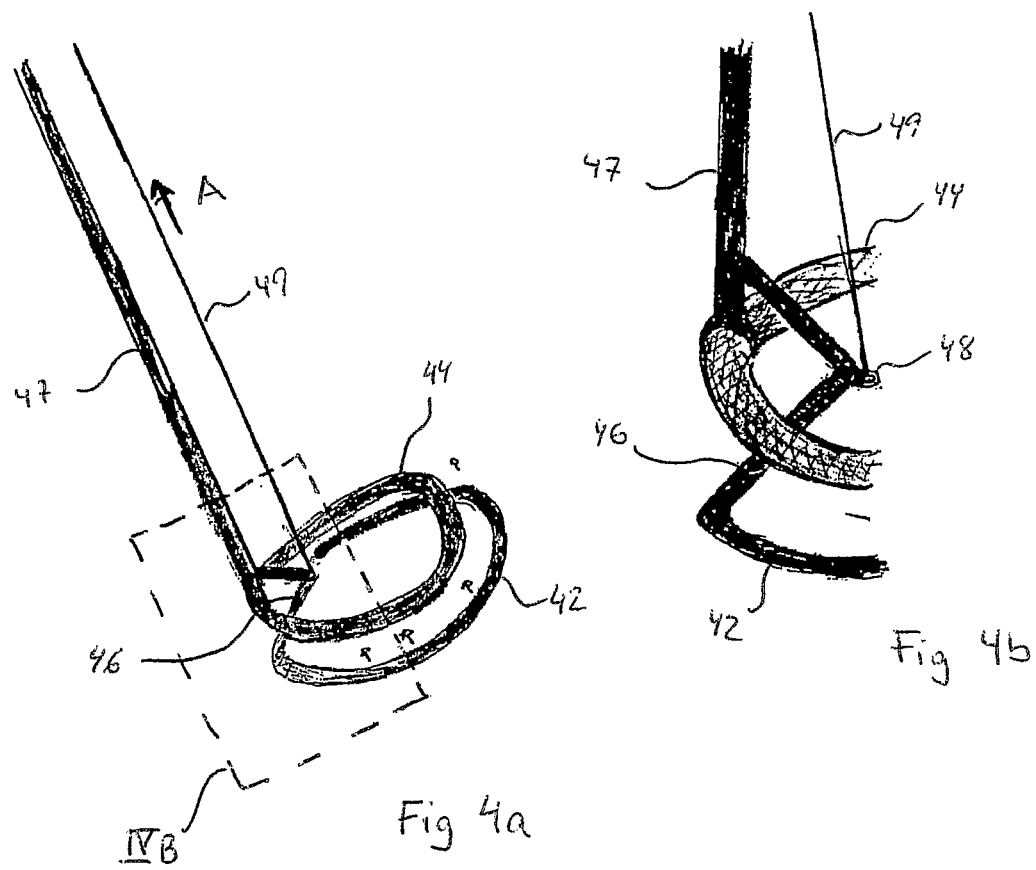

ANNULOPLASTY INSTRUMENT

FIELD OF THE INVENTION

The present invention generally relates to heart valve repair and replacement techniques and annuloplasty devices. More specifically, the invention relates to the replacement of heart valves.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak (insufficiency). The leaflets and chords may become calcified and thickened rendering them stenotic (obstructing forward flow). Finally, the valve relies on insertion of the chordae inside the ventricle. If the ventricle changes in shape, the valve support may become non-functional and the valve may leak.

Mitral and tricuspid valve replacement and repair are traditionally performed with a suture technique. During valve replacement, sutures are spaced around the annulus (the point where the valve leaflet attaches to the heart) and then the sutures are attached to a prosthetic valve. The valve is lowered into position and when the sutures are tied, the valve is fastened to the annulus. The surgeon may remove all or part of the valve leaflets before inserting the prosthetic valve. In valve repair, a diseased valve is left in situ and surgical procedures are performed to restore its function. Frequently an annuloplasty ring is used to reduce the size of the annulus. The ring serves to reduce the diameter of the annulus and allow the leaflets to oppose each other normally. Sutures are used to attach a prosthetic ring to the annulus and to assist in plicating the annulus.

In general, the annuloplasty rings and replacement valves must be sutured to the valve annulus and this is time consuming and tedious. If the ring is severely malpositioned, then the stitches must be removed and the ring repositioned relative to the valve annulus during restitching. In other cases, a less than optimum annuloplasty may be tolerated by the surgeon rather than lengthening the time of the surgery to restitch the ring.

During heart surgery, a premium is placed on reducing the amount of time used to replace and repair valves as the heart is frequently arrested and without perfusion. It would therefore be very useful to have a method to efficiently attach a prosthesis into the mitral or tricuspid valve position.

SUMMARY OF THE INVENTION

It is an object of the invention to provide a more reliable and more easily accomplished valve repair or replacement. It is a specific object of the invention to facilitate insertion of an annuloplasty implant.

These and other objects of the invention are accomplished by means of a device and a method according to the independent claims. Preferred embodiments of the invention are apparent from the dependent claims.

Thus, according to a first aspect of the invention, a replacement valve device for replacing a heart valve of a patient is provided. The device comprises an implantation instrument, which comprises a first support ring, and a second support ring connected to said first support ring to form a coiled configuration. The first support ring is configured to abut one side of an area of valve tissue and the second support ring is configured to abut an opposite side of the area of the valve tissue to thereby trap the valve tissue therebetween. The device further comprises a replacement valve adapted to be attached to the valve tissue and including at least one valve element for allowing and preventing blood flow through the valve position. The replacement valve is coupled to the implantation instrument for insertion into the patient.

The invention also provides a method of replacing a heart valve of a patient. The method comprises inserting an implantation instrument comprising a first and a second support ring connected to each other to form a coiled configuration and a replacement valve being attached to the second support ring into the patient, said instrument being inserted such that valve tissue is trapped between the first and second support rings, attaching the replacement valve to the valve tissue, and removing the implantation instrument.

The implantation instrument provides a possibility to easily introduce the device into position in a heart valve. The implantation instrument anchors the device at the heart valve position such that the replacement valve may be attached to valve tissue that is fixated by the implantation instrument. The replacement valve may be arranged to be attached to the valve tissue by means of staples. This implies that the replacement valve may be easily attached to the valve tissue, when the implantation instrument fixates the valve tissue.

The replacement valve may be coupled to the second support ring in a removable manner. This implies that the replacement valve may be detached from the implantation instrument after the replacement valve has been attached to the valve tissue. The implantation instrument may thereafter be removed from the patient. The annuloplasty implant may be attached to the second support ring by means of a removable suture. The suture may be cut in order to detach the annuloplasty implant from the implantation instrument.

The first and second support rings may be axially moveable with respect to each other. This facilitates insertion of the annuloplasty instrument. The rings may initially be applied on opposite sides of valve tissue and may thereafter be drawn towards each other in order to trap valve tissue therebetween. Thus, there is no friction between the rings and valve tissue during placement of the rings on opposite sides of the valve.

The step of inserting may comprise inserting a first end of the first support ring through a portion of the valve tissue, rotating the implantation instrument to position the first support ring on a first side of the valve, and positioning the second support ring on an opposite second side of the valve. The first and second support ring are thus easily applied on opposite sides of the valve.

According to a second aspect of the invention, a device is provided for repairing a heart valve comprised of valve tissue including an annulus and a plurality of leaflets for allowing and preventing blood flow through a patient's heart. The device comprises an implantation instrument, which comprises a first support ring, and a second support ring connected to the first support ring to form a coiled configuration. The first support ring is configured to abut one side of the valve and the second support ring is configured to abut an opposite side of the valve to thereby trap a portion of the valve tissue, that is, annulus tissue and/or leaflet tissue, therebetween. The device further comprises an annuloplasty implant adapted to be attached to the heart valve annulus in order to reshape the annulus and allow the leaflets to open and close properly.

The implantation instrument is applied to the heart valve in a much easier manner than conventionally utilized annuloplasty rings. By means of the implantation instrument it is possible to fixate the valve annulus and primarily reshape it. This primary reshaping of the valve annulus facilitates attachment of the annuloplasty implant to the valve annulus. There is merely a need for a slight further reshaping of the valve annulus by the attachment of the annuloplasty implant in order to achieve the desired shape of the valve annulus. Since the attachment of the annuloplasty implant need not dramatically change the shape of the valve annulus, the possibility of correctly positioning the annuloplasty implant is greatly increased. This implies that there is a very slim risk that the annuloplasty implant will need to be repositioned. Further, by means of the device the desired reshaping of the valve annulus may in most cases be achieved.

The invention contemplates various embodiments of the device, including embodiments for catheter-based surgery and embodiments for open heart surgery.

The first and second support rings may have generally triangular-shaped cross sections with flat sides opposing one another and trapping valve tissue therebetween.

At least the opposed surfaces of the first and second support rings may be roughened, such as by the use of fabric, coatings, knurling or the like to facilitate better engagement and retention of the support rings on the valve tissue. The opposed surfaces may be roughened in a pattern extending along the longitudinal direction of the rings. This implies that the roughened surface will serve to prevent slippage of tissue through the ring while presenting a low friction for the ring to be turned into position abutting the valve. The implantation instrument may have an inherent shape where the first and second rings contact or nearly contact each other. Thus, the implantation instrument will present a spring force pushing the first and second rings towards each other. The spring force will make the first and second rings fixating valve tissue between them.

Preferably, the first and second support rings are formed integrally from a coiled rod, such as a metallic rod, with one end of the rod formed as a leading end and one end formed as a trailing end. These ends may be bent in opposite directions so that the leading end may be directed through the valve tissue and the trailing end may be grasped by an appropriate surgical implement. A carrier may be used to rotate the implantation instrument into position on opposite sides of the valve annulus. As another alternative, the carrier may be coil-shaped and the implantation instrument may be rotated into place on only one side of the valve annulus similar to conventional rings. The carrier may also be rotated in opposite direction for withdrawing the implantation instrument. The first and second support rings may be adjustable in diameter to allow adjustment of the valve annulus.

The annuloplasty implant may have an arcuate shape conforming to a desired arcuate shape of a portion of the annulus. The annuloplasty implant may then be attached to the portion of the valve annulus for reshaping the valve annulus. The desired reshaping of the valve annulus may be achieved by the annuloplasty implant reshaping only a portion of the valve annulus. Thus, the annuloplasty implant may be C- or U-shaped. The annuloplasty implant may alternatively have a ring-shape conforming to the desired shape of the annulus. The annuloplasty implant may thus be attached to the valve annulus forcing it to assume the desired shape.

The annuloplasty implant may be removably attached to the second support ring of the implantation instrument. The annuloplasty implant may then be detached from the implantation instrument after being attached to the valve annulus. The implantation instrument may thereafter be removed from the patient. The annuloplasty implant may be attached to the second support ring by means of a removable suture. The suture may be cut in order to detach the annuloplasty implant from the implantation instrument.

According to a third aspect of the invention, a kit is provided for repairing a heart valve comprised of valve tissue including an annulus and a plurality of leaflets for allowing and preventing blood flow. The kit comprises an implantation instrument, which comprises a first support ring, and a second support ring connected to the first support ring to form a coiled configuration. The first support ring is configured to abut one side of the valve and the second support ring is configured to abut an opposite side of the valve to thereby trap a portion of the valve tissue therebetween. The kit further comprises an annuloplasty implant adapted to be attached to the heart valve annulus in order to reshape the annulus and allow the leaflets to open and close properly.

The annuloplasty implant need not be attached to the implantation instrument for being inserted to the heart valve. The implantation instrument may provide the primary reshaping of the valve annulus. The annuloplasty implant may then be separately inserted to permanently reshape the valve annulus. The correct positioning of the annuloplasty implant is now easily achieved since the primary reshaping of the valve annulus provided by the implantation instrument clearly indicates how the annuloplasty implant should be attached to the valve annulus.

According to a fourth aspect of the invention, a method is provided for repairing a heart valve comprised of valve tissue including an annulus and a plurality of leaflets for allowing and preventing blood flow. The method comprises inserting an implantation instrument comprising a first and a second support ring connected to each other to form a coiled configuration, said instrument being inserted such that valve tissue is trapped between the first and second support rings, attaching an annuloplasty implant to the annulus in order to reshape it, and removing the implantation instrument.

The step of inserting the instrument may comprise temporarily reshaping the annulus to facilitate attachment of the annuloplasty implant to the annulus. Thus, the implantation instrument will guide the positioning of the annuloplasty implant.

The step of inserting may further comprise inserting a first end of the first support ring through a portion of the valve tissue, rotating the implantation instrument to position the first support ring on a first side of the valve, and positioning the second support ring on an opposite second side of the valve. The first and second support ring are thus easily applied on opposite sides of the valve.

Various additional objectives, advantages and features of the invention will become more readily apparent to those of ordinary skill in the art upon review of the detailed description of the illustrative embodiments.

BRIEF DESCRIPTION OF THE DRAWINGS

FIGS. 4a-b are perspective views of a device according to another embodiment of the invention. FIG. 4b is an enlarged view of the portion marked IVB in FIG. 4a.

DETAILED DESCRIPTION OF THE PREFERRED EMBODIMENTS

Figure 1:
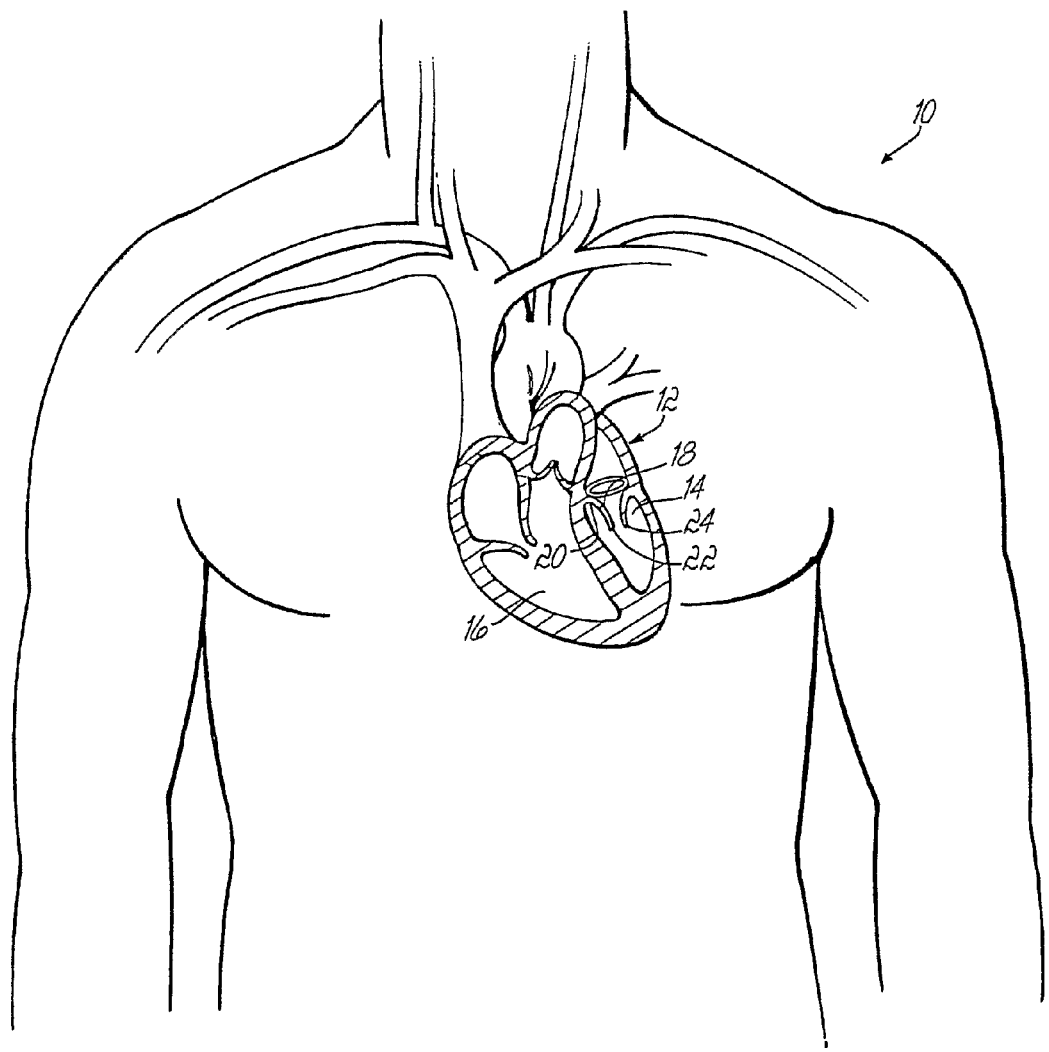
FIG. 1 schematically illustrates a patient with a heart shown in cross section and a device of the present invention schematically illustrated as supporting the mitral valve.
Figure 1A:
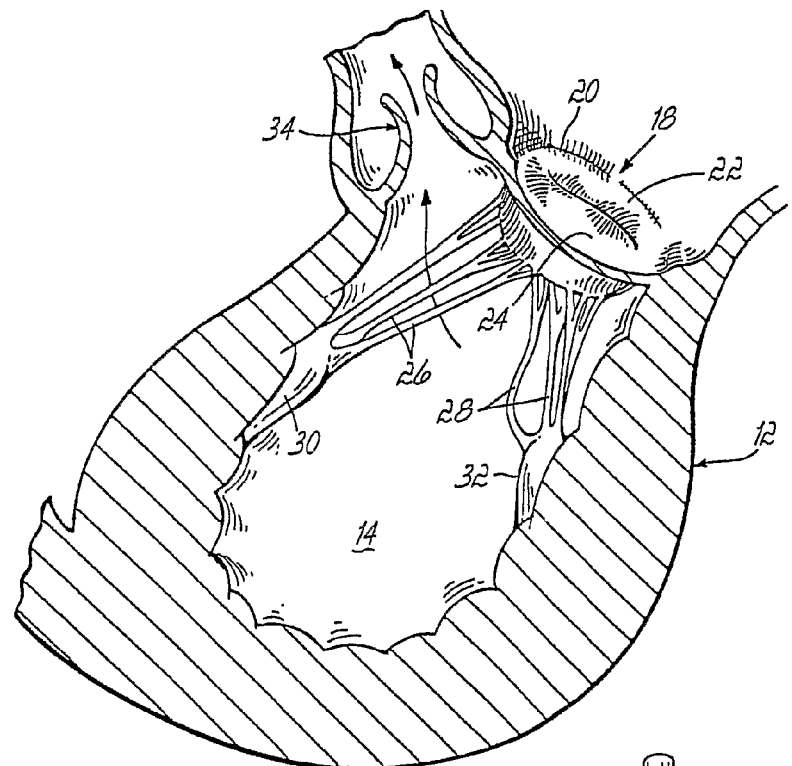
FIG. 1A is a cross sectional view of the left ventricle showing the mitral valve and a device according to a first embodiment of the invention in perspective.

FIG. 1 illustrates a patient 10 having a heart 12 shown in cross section including a left ventricle 14 and a right ventricle 16. The concepts of the present invention are suitable to be applied, for example, to a mitral valve 18 which supplies blood into left ventricle 14. Mitral valve 18, as better shown in FIG. 1A, includes an annulus 20 and a pair of leaflets 22, 24 which selectively allow and prevent blood flow into left ventricle 14. It will be appreciated that the term annulus tissue is used extensively throughout this disclosure in reference to the drawings, however, the inventive principles are equally applicable when referring to other valve tissue such as leaflet tissue or other attached vessel tissue. Leaflets 22, 24 are supported for coaptation by chordae tendinae or chords 26, 28 extending upwardly from respective papillary muscles 30, 32. Blood enters left ventricle 14 through mitral valve 18 and is expelled during subsequent contraction of heart 12 through aortic valve 34. It will be appreciated that the present invention is applicable to tricuspidal heart valves as well.

Figure 3:
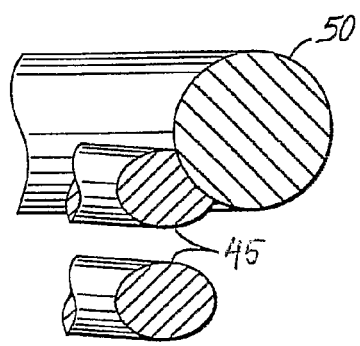
FIG. 3 is a cross sectional view of the device in FIG. 2.
Figure 2:
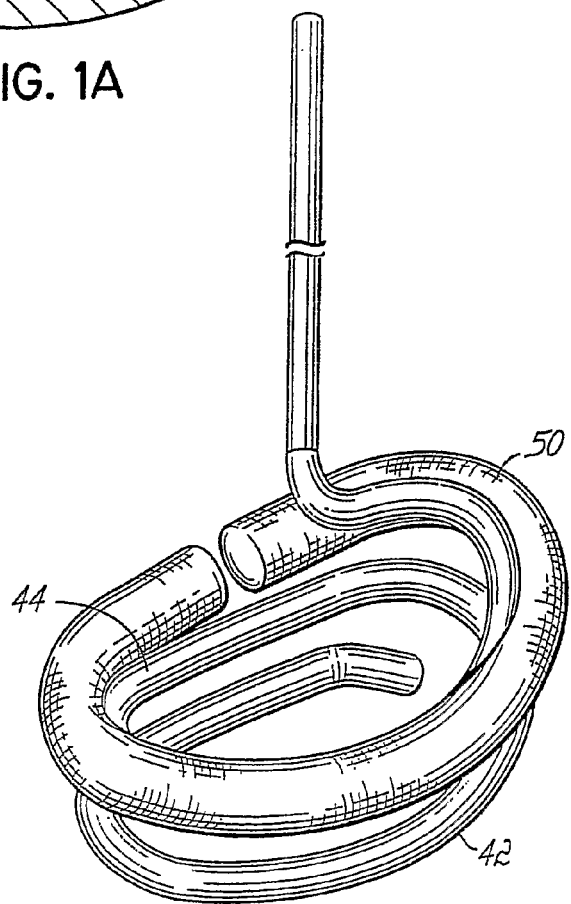
FIG. 2 is a perspective view of a device according to an embodiment of the invention.

A preferred device of the present invention is shown in FIGS. 2 and 3. The device comprises an implantation instrument 40 which comprises a first and a second support ring 42, 44 assuming a coiled configuration in the form of a spiral or keyring-type configuration. Any suitable medical grade material(s), such as medical grade metals or plastics, may be used to form the implantation instrument 40. The device is shown in cross section in FIG. 3. The implantation instrument 40 has a traditional cross sectional shape associated with a keyring. In this embodiment flat, opposed surfaces 45 are arranged to trap valve annulus tissue 20 therebetween. The opposed surfaces 45 may also be roughened in order to improve engagement with the valve annulus 20.

As illustrated in FIGS. 4a-b, the first and second support rings 42, 44 may be axially moved in relation to each other. Thus, the support rings 42, 44 may be inserted on opposite sides of a heart valve and thereafter be drawn towards each other for trapping valve annulus tissue 20 between them. The first support ring 42 is connected to the second support ring 44 via a rod 46. The rod 46 is attached to the first support ring 42 and is connected to a stem 47 that extends from the second support ring 44 out of the patient in which the implantation instrument is inserted. The rod 46 is slidably connected to the stem 47 for moving the first support ring 42 in axial relation to the second support ring 44. The rod 46 is angled in order to allow the first and second support rings 42, 44 to be arranged in close relationship to each other. The rod 46 comprises an eye 48 at its angle. The eye 48 may receive a string 49 extending out of the patient. The implantation instrument 40 may be inserted into the patient in the configuration shown in FIG. 4a and in greater detail in FIG. 4b. The instrument 40 may then be rotated into position with the support rings 42, 44 on opposite sides of a hear valve. The rotational movement will not be hindered by friction between the support rings 42, 44 and annulus tissue 20 since the support rings 42, 44 are spaced from each other. When the support rings 42, 44 have been placed at opposite sides of the heart valve, the first support ring 42 may be drawn towards the second support ring 44 by pulling the string 49, as indicated by arrow A.

An annuloplasty implant 50 is attached to the second support ring 44 of the implantation instrument 40, by means of sutures or clips. The annuloplasty implant 50 may be any type of annuloplasty ring, such as the CG Future™ Annuloplasty System manufactured by Medtronic, Inc., the SJM Tailor® Annuloplasty Ring or the SJM Tailor® Flexible Annuloplasty Band manufactured by St. Jude Medical, Inc., the Sovering™ manufactured by Sorin Group, the Carpentier-McCarthy-Adams IMR ETlogix Annuloplasty Ring® or the Carpentier-Edwards Classic Annuloplasty Ring® manufactured by Edwards Lifesciences Corporation, which annuloplasty ring may form a complete ring-shape or an arcuate shape. The annuloplasty implant 50 is adapted to be attached to the valve annulus 20 by means of suture threads, as will be explained in further detail below. The annuloplasty implant 50 has a shape conforming to a desired shape of the valve annulus 20. Thus, when attached to the valve annulus 20, the annuloplasty implant 50 will reshape the valve annulus 20 to a desired shape. The annuloplasty implant 50 is non-stretchable lengthwise, which implies that when attached to the valve annulus it will not allow dilatation of the annulus. However, the annuloplasty implant may be flexible to change its shape while maintaining its length to allow the normal movements of the valve annulus 20 during a heart cycle. The annuloplasty implant 50 may have sections of differing rigidity and flexibility to comply with the normal movements of the valve annulus 20 during the heart cycle.

Figure 5:
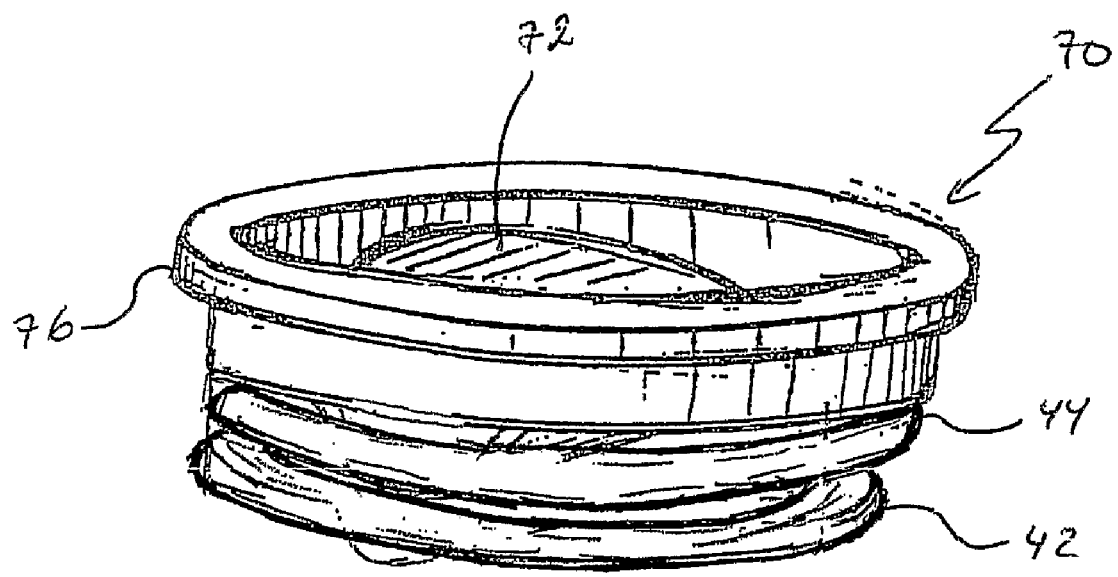
FIG. 5 is a perspective view of a device according to a second embodiment of the invention.
Figure 6A:
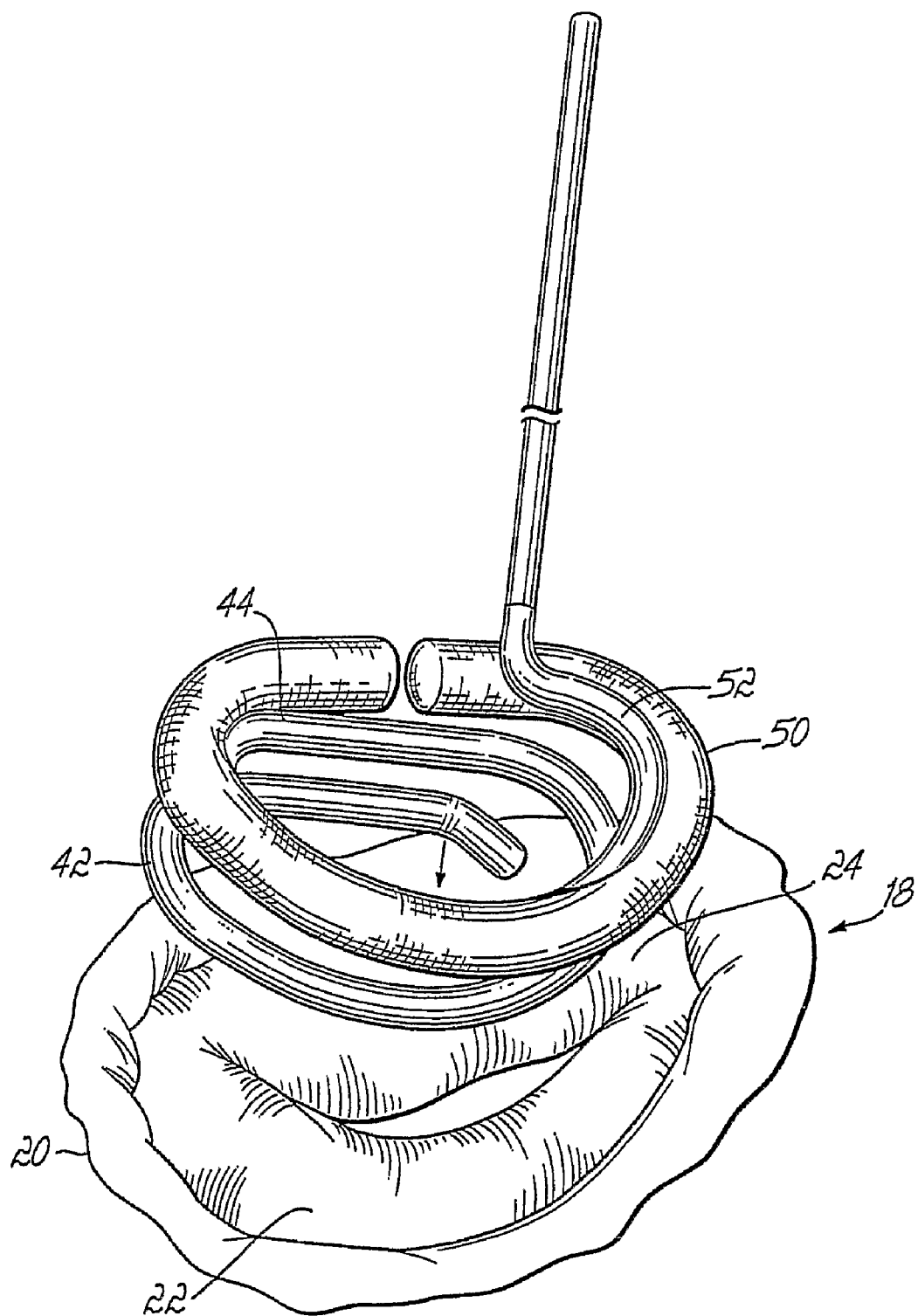
FIGS. 6a-b are partially sectioned perspective views of the mitral valve and the device of the invention during implantation of an annuloplasty implant of the device.
Figure 6B:
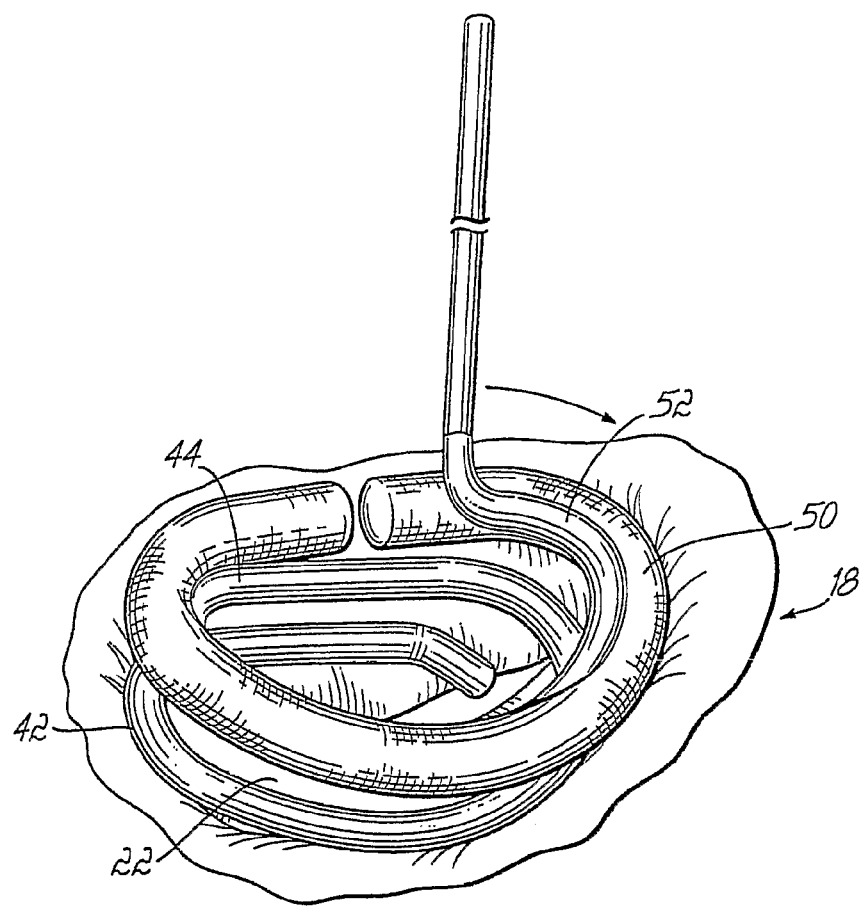

Alternatively, as illustrated in FIG. 5, a replacement valve 70 is attached to the second support ring 44 of the implantation instrument 40, by means of sutures or clips. The replacement valve 70 may be conventional or of any desired design. The replacement valve 70 may have movable flaps 72, 74 for providing a valve function. The replacement valve 70 further has an outer portion 76 at least partly surrounding the flaps 72, 74 and arranged to be attached to annulus tissue 20. The outer portion 76 may be a cuff or flange arranged to receive a suture or staple or any other means for attaching the outer portion 76 to the annulus tissue 20. The implantation instrument 40 is arranged to fixate the annulus tissue 20 for facilitating attachment of the replacement valve 70 to the annulus tissue 20.

Figure 7:
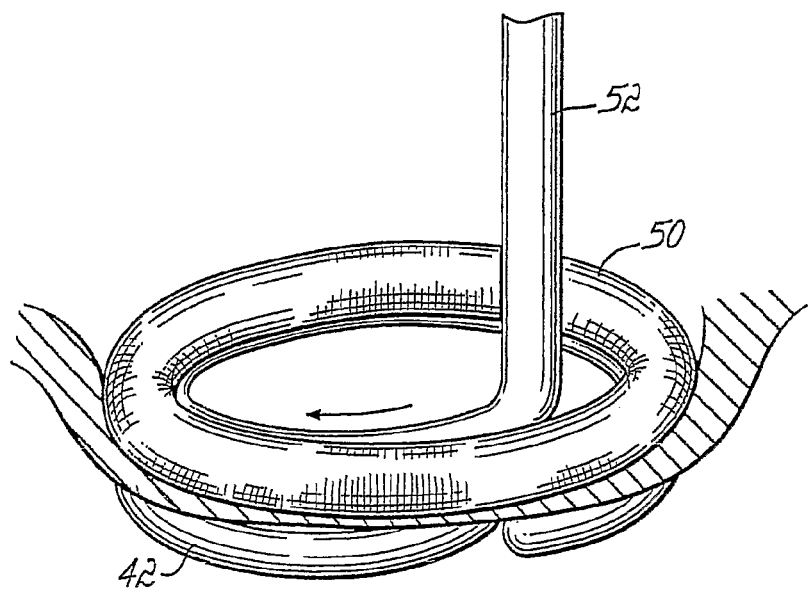
FIG. 7 is a partially sectioned perspective view showing the device of the invention when the implantation instrument has been turned into position.

Referring now to FIGS. 6-9, a method for repairing a heart valve by means of the device will be described. First, access to the heart valve is achieved by conventional techniques, including arresting the heart and opening the chest. In FIG. 6a, the device is shown when being inserted to the mitral valve 18. The implantation instrument 40 is being carried on a coil-shaped carrier 52, which is connected to a stem for remote control of the positioning of the carrier 52. An end of the first support ring 42 is brought to a corner of the opening between the leaflets 22, 24 of the mitral valve 18, as shown in FIG. 6b. The end is led through the opening and the coil-shaped carrier 52 is turned 360 degrees. Thus, the first support ring 42 will be rotated into place on one side of the valve 18, whereas the second support ring 44 is placed on the opposite side of the valve 18. In this way, the implantation instrument 40 is arranged in engagement with the valve 18, as shown in FIG. 7. Alternatively, the implantation instrument 40 shown in FIG. 4a may be inserted. The implantation instrument 40 is rotated into position and, thereafter, the first support ring 42 is drawn towards the second support ring 44 so that the instrument 40 is arranged in engagement with the valve.

Figure 8:
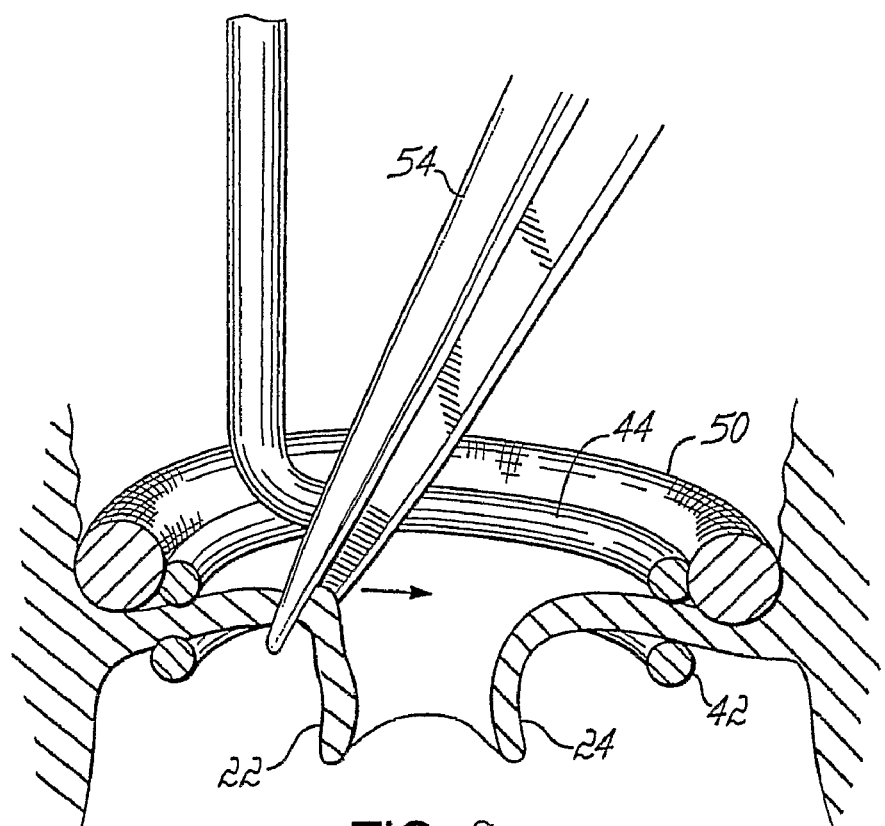
FIG. 8 is a cross-sectional view illustrating primary reshaping of the valve.

The leaflets 22, 24 may now be drawn towards each other through the pinch of the support rings 42, 44, as illustrated in FIG. 8. The leaflets are drawn through the pinch by means of a forceps instrument 54. The support rings 42, 44 may flex away from each other to allow drawing leaflets 22, 24 through the pinch and towards each other for preventing the leaflets 22, 24 to slip back. The valve annulus 20 may in this way be reshaped and be temporarily held in the new shape by means of the implantation instrument 40. The support rings 42, 44 may have roughened, opposed surfaces 45 to better keep the leaflets 22, 24 from slipping through the pinch and to hold the valve annulus 20 in its reshaped form.

Figure 9:
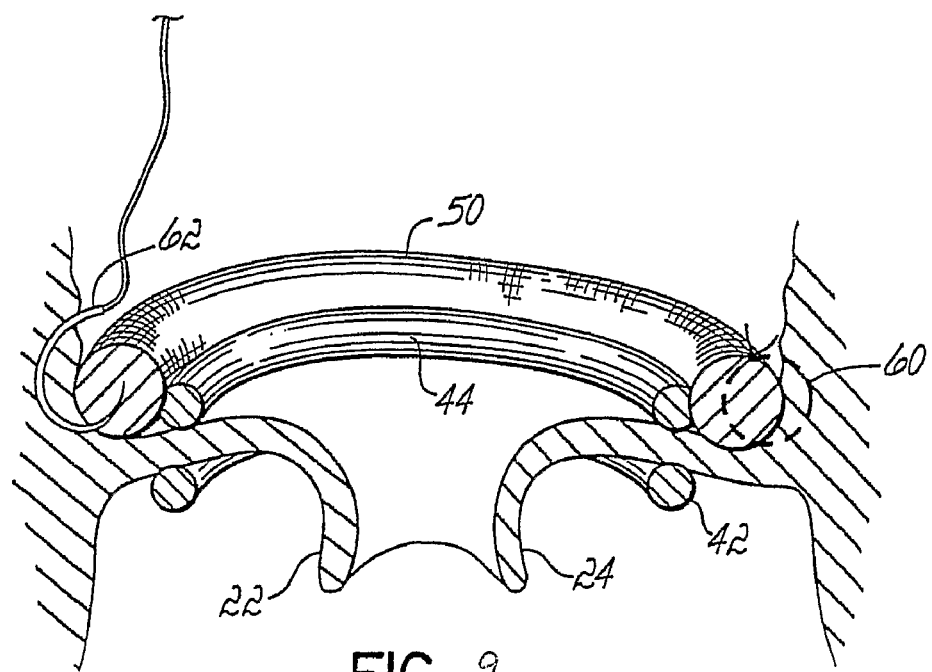
FIG. 9 is a partially sectioned perspective view showing the device when the annuloplasty implant is being attached to the valve annulus.

The annuloplasty implant 50, which has been carried into position by means of the second support ring 44, may now be attached to the valve annulus 20 for achieving a permanent reshaping of the annlus 20. Since a primary reshaping has already been made, the positioning of the annuloplasty implant 50 is facilitated. The annuloplasty implant 50 is sutured to the valve annulus, as illustrated in FIG. 9, showing a completed suture 60 attaching the annuloplasty implant 50 to the valve annulus 20 and showing a suture 62 being performed. In this way, the annuloplasty implant 50 is firmly attached to the valve annulus 20 for keeping the valve annulus 20 in its reshaped form. The leaflets 22, 24 may also or alternatively be drawn towards each other through the pinch of the support rings 42, 44 during suturing of the annuloplasty implant 50.

Figure 10:
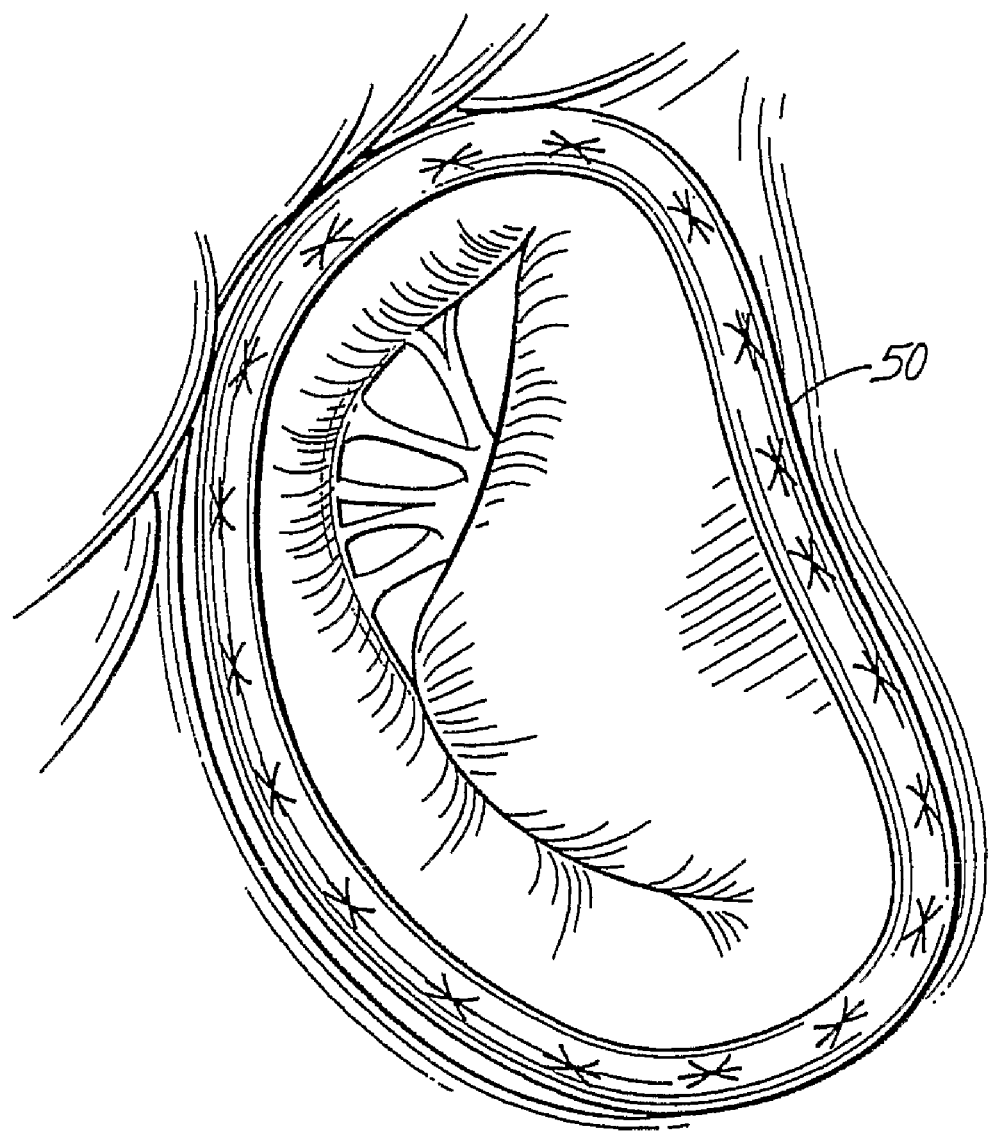
FIG. 10 is a perspective view showing the device after implantation is completed.

When the annuloplasty implant 50 has been firmly attached to the valve annulus 20, the annuloplasty implant 50 is released from the implantation instrument 40. The sutures holding the annuloplasty implant 50 attached to the second support ring 44 are cut in order to release the annuloplasty implant 50 from the implantation instrument 40. Now, the implantation instrument 40 may be withdrawn. The carrier 52 is turned 360 degrees in order to rotate the first support ring 42 to be retracted through the opening between the leaflets 22, 24. Thereafter, the carrier 52 with the implantation instrument 40 may be retracted from the patient. As shown in FIG. 10, the annuloplasty implant 50 is now left in the patient holding the valve annulus 20 in a reshaped form such as to function normally.

As an alternative, the implantation instrument 40 does not carry the annuloplasty implant 50. In this case, the implantation instrument 40 is inserted into position first. This positioning of the implantation instrument 40 may be performed as described above with reference to FIGS. 6-8. While the implantation instrument 40 is held in place maintaining the temporary reshaping of the valve annulus 20, the annuloplasty implant 50 may be inserted to the mitral valve by means of conventional techniques for inserting an annuloplasty ring using a carrier. The annuloplasty implant 50 is then sutured to the valve annulus in order to permanently keep the valve annulus 20 in its reshaped form. Thereafter, the carrier used for inserting the annuloplasty implant 50 and the implantation instrument 40 may be withdrawn leaving the annuloplasty implant 50 in the patient.

Figure 11:
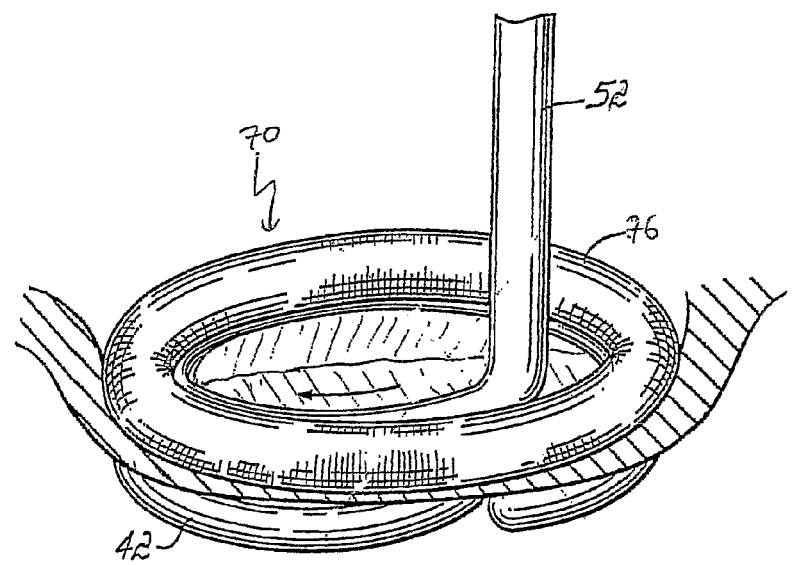
FIG. 11 is a partially sectioned perspective view showing the device according to the second embodiment when the implantation instrument has been turned into position.
Figure 12:
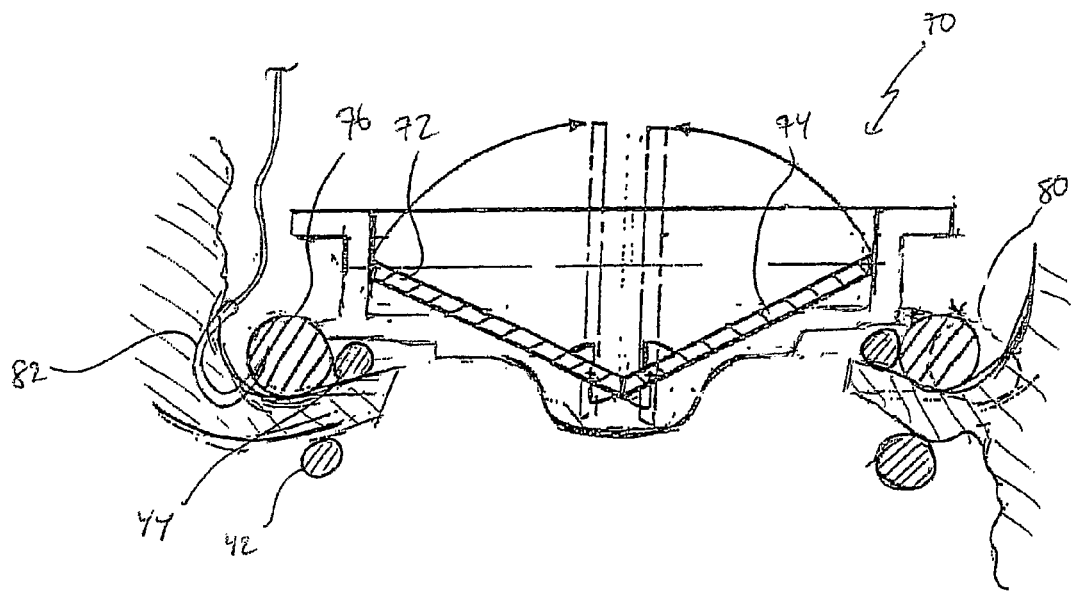
FIG. 12 is a partially sectioned perspective view showing the device when the replacement valve is being attached to the valve annulus.
Figure 13:
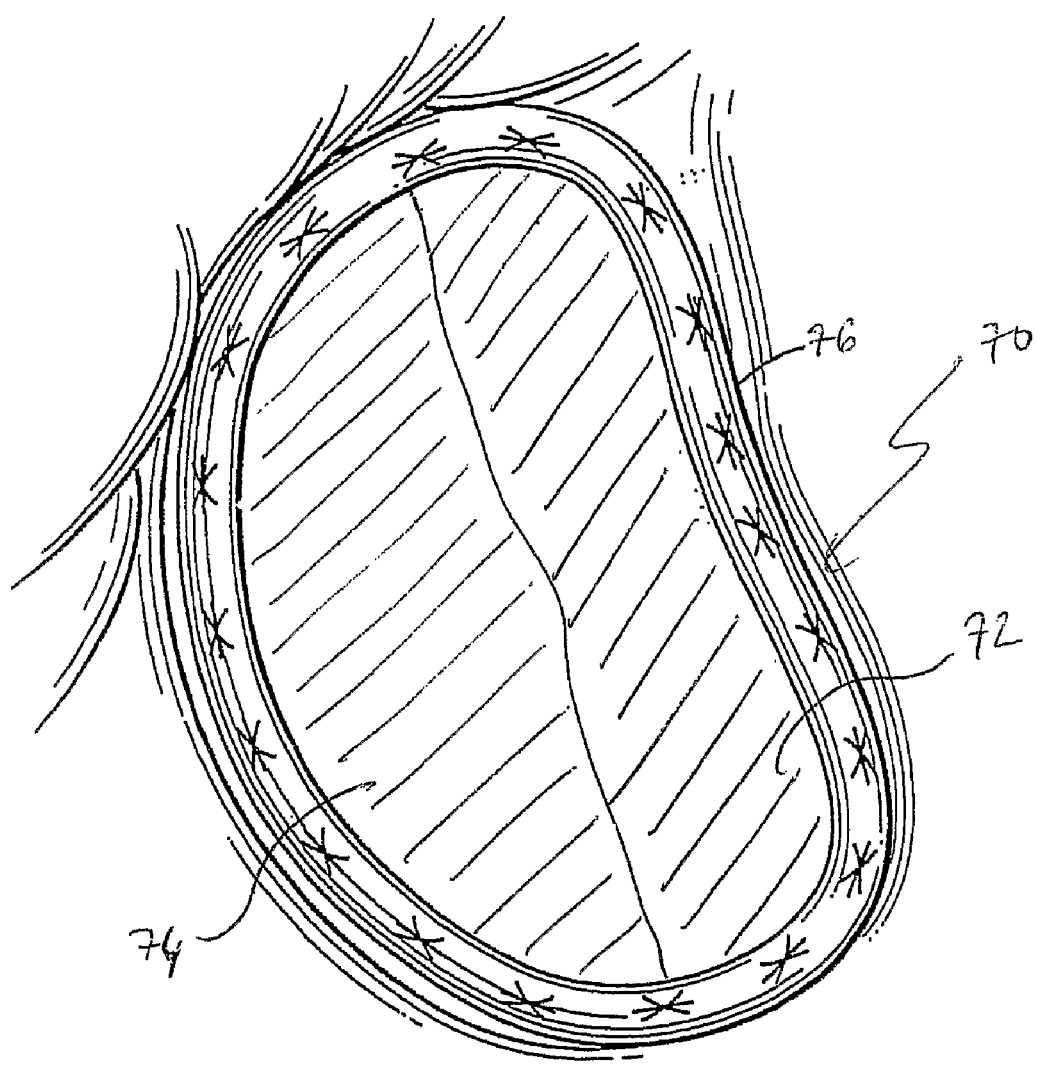
FIG. 13 is a perspective view showing the device according to the second embodiment after implantation is completed.

Referring now to FIGS. 11-13, a method for replacing a mitral valve by means of the device will be described. First, the native leaflets 22, 24 are cut off and removed, since the function of the leaflets 22, 24 will be replaced by a replacement valve 70. Then, the implantation instrument 40 may be inserted in a manner similar to the insertion described with reference to FIGS. 6a-6b above. As shown in FIG. 11, the implantation instrument is arranged in engagement with the valve 18.

The replacement valve 70, which has been carried into position by means of the second support ring 44, may now be attached to the valve annulus 20 for achieving a permanent replacement of the valve function. Since the support rings 42, 44 are arranged trapping annulus tissue 20 therebetween, the implantation instrument 40 will fix or stabilize the shape and position of the valve annulus 20. The support rings 42, 44 may have roughened, opposed surfaces 45 to better maintain the shape of the valve annulus 20. Thus, attachment of the replacement valve 70 to the valve tissue is facilitated as the tissue is held in position. For instance, the replacement valve 70 may be stapled to the valve tissue, while the implantation instrument 40 provides an anvil to the staple. Alternatively, the replacement valve 70 is sutured to the valve annulus, as illustrated in FIG. 12, showing a completed suture 80 attaching the replacement valve 70 to the valve annulus 20 and showing a suture 82 being performed. In this way, the replacement valve 70 is firmly attached to the valve annulus 20 for providing a valve function.

When the replacement valve 70 has been firmly attached to the valve annulus 20, the replacement valve 70 is released from the implantation instrument 40. The sutures holding the replacement valve 70 attached to the second support ring 44 are cut in order to release the replacement valve 70 from the implantation instrument 40. Now, the implantation instrument 40 may be withdrawn. The carrier 52 is turned 360 degrees in order to rotate the first support ring 42 to be retracted through the opening between the leaflets 22, 24. Thereafter, the carrier 52 with the implantation instrument 40 may be retracted from the patient. As shown in FIG. 13, the replacement valve 70 is now left in the patient replacing the function of the native valve.

It should be emphasized that the preferred embodiments described herein are in no way limiting and that many alternative embodiments are possible within the scope of protection defined by the appended claims.

For example, the access to the heart valve may be achieved endoscopically. In such case, the implantation instrument 40 and the annuloplasty implant 50 need to be inserted through a narrow tube (endoscope). This implies that the implantation instrument 40 and the annuloplasty implant 50 will need to be compressed during insertion in order to pass through the endoscope. The implantation instrument 40 needs to assume its proper shape after having been passed through the endoscope. Therefore, using an endoscopic approach, the implantation instrument 40 should preferably be formed from a shape memory material. This allows the implantation instrument 40 to be compressed and also to have a stable shape when being applied to the heart valve. Further, the annuloplasty implant 50 needs to be flexible in order to be compressed for the insertion through the endoscope.

The invention claimed is:

1. A valve replacement device for replacing a native heart valve of a patient, the device comprising:
 a) an implantation instrument, comprising:
  a first support ring, and a second support ring connected to said first support ring in a form of a coiled configuration, said first support ring configured to abut a first side of an area of heart valve tissue of the heart valve and said second support ring configured to abut a second side, opposite to said first side, of the area of the heart valve tissue to thereby temporarily trap the valve tissue between said first support ring and said second support ring; and b) a replacement valve adapted to be attached to said heart valve tissue of the native valve and including at least one valve element for allowing and preventing blood flow through the valve position; wherein said replacement valve is in a removable manner coupled to the second support ring of said implantation instrument for insertion into the heart valve, and whereby said implantation instrument is configured to temporarily engage the heart valve and to fix or stabilize a shape and position of said trapped heart valve tissue for facilitating attachment of the replacement valve to the heart valve tissue, and wherein said replacement valve is further adapted to be released from said implantation instrument leaving the replacement valve attached to the heart valve tissue, and said implantation instrument is configured to be retracted from the patient when said replacement valve is attached to the heart valve tissue.

2. The device according to claim 1, wherein the replacement valve is attached to the second support ring by means of a removable suture for insertion into the heart valve.

3. The device according to claim 1, wherein the replacement valve is arranged to be attached to the valve tissue by means of staples.

4. The device according to claim 1, wherein the first and second support rings are axially moveable with respect to each other.

5. The device according to claim 1, wherein said first support ring is connected to said second support ring via a rod that is attached to said first support ring and connected to a stem that extends from the second support ring, wherein said rod is slidably connected to the stem for moving the first support ring axially in relation to the second support ring.

6. The device according to claim 5, wherein said rod is angled in order to allow the first and second support rings to be arranged in close relationship to each other.

7. The device according to claim 5, wherein the rod comprises an eye at its angle for receiving a string extending out of the patient, whereby, when the first and second support rings have been placed at said opposite sides of the heart valve, the first support ring is arranged to be drawn towards the second support ring by pulling the string.

8. The device according to claim 1, wherein said the first and second support rings are formed integrally from a coiled rod.

9. The device according to claim 1, comprising a carrier adapted to rotate the implantation instrument into position in a first rotational direction and adapted to withdraw the implantation instrument by rotation in a second rotational direction that is opposite said first rotational direction.

10. The device according to claim 1, wherein said implantation instrument has an inherent shape where the first and second rings contact or nearly contact each other, and wherein the implantation instrument has a spring force pushing the first and second rings towards each other for trapping said heart valve tissue between them.

11. The device according to claim 1, wherein said implantation instrument is adapted to be rotated into position on said opposite sides of said heart valve.

12. The device according to claim 1, wherein a first end of the first support ring is adapted to be inserted through a portion of the valve tissue, and the implantation instrument is adapted to be rotated to position the first support ring on the first side of the valve the second support ring on the opposite second side of the valve.

13. The device according to claim 1, wherein said first and second support rings are formed from a shape memory alloy.

14. The device according to claim 1, wherein the implantation instrument further comprises a material on at least one of said first and second support rings for reducing friction between the respective rings and the valve tissue in the longitudinal direction of the rings.

15. The device according to claim 1, wherein opposed surfaces of said first and second support rings are roughened to facilitate engagement with the valve tissue.

16. The device according to claim 1, further comprising a coating of cushioning material on said first support ring and said second support ring.

17. The device according to claim 1, wherein said support rings are formed from a flat plate material.

18. The device according to claim 1, wherein said first and second support rings are adjustable in diameter to allow adjustment of the heart valve tissue.

19. The device according to claim 1, wherein said heart valve tissue includes an annulus, and wherein leaflets of said native heart valve are removed.

* * * * *

UNITED STATES PATENT AND TRADEMARK OFFICE
CERTIFICATE OF CORRECTION

PATENT NO. : 7,951,195 B2  
APPLICATION NO. : 11/667335  
DATED : May 31, 2011  
INVENTOR(S) : Per Antonsson et al.

Page 1 of 1

It is certified that error appears in the above-identified patent and that said Letters Patent is hereby corrected as shown below:

On the Title Page

Please insert the following after item (65) Prior Publication Data
--US 2008/0033542 A1  Feb. 7, 2008-- item --(30) Non-Provisional application No. 10/992,998, filed on November 19, 2004, now Pat. No. 7,077,861.--

Signed and Sealed this
Twenty-fourth Day of February, 2015

Michelle K. Lee
*Deputy Director of the United States Patent and Trademark Office*